United States Patent [19]

Carusillo et al.

[11] Patent Number: 5,207,697
[45] Date of Patent: May 4, 1993

[54] BATTERY POWERED SURGICAL HANDPIECE

[75] Inventors: Steven J. Carusillo, Kalamazoo; David H. Grulke, Battle Creek, both of Mich.

[73] Assignee: Stryker Corporation, Kalamazaoo, Mich.

[21] Appl. No.: 722,011

[22] Filed: Jun. 27, 1991

[51] Int. Cl.$^5$ .............................. A61B 17/32
[52] U.S. Cl. ..................... 606/167; 606/80; 320/2
[58] Field of Search ............ 606/80, 81, 180, 167; 320/2; 310/50

[56] References Cited

U.S. PATENT DOCUMENTS

| | | | |
|---|---|---|---|
| 3,120,845 | 2/1964 | Horner | 606/80 |
| 3,999,110 | 12/1976 | Ramstrom et al. | 320/2 |
| 4,679,557 | 7/1987 | Opie et al. | 606/180 |
| 4,728,876 | 3/1988 | Mongeon et al. | |
| 4,751,452 | 6/1988 | Kilmer et al. | 310/50 |
| 4,835,410 | 5/1989 | Bhagwat et al. | 310/50 |
| 4,873,461 | 10/1989 | Brennan et al. | |
| 5,026,384 | 6/1991 | Farr et al. | 606/180 |
| 5,089,738 | 2/1992 | Bergquist et al. | 310/50 |

OTHER PUBLICATIONS

Drawing of cross-sectional view of prior Model 2102.
Brochure entitled "New OrthoPower 90 cordless instruments" of Stryker Corporation.

Primary Examiner—C. Fred Rosenbaum
Assistant Examiner—Manual Mendez
Attorney, Agent, or Firm—Flynn, Thiel, Boutell & Tanis

[57] ABSTRACT

A pistol-shaped surgical handpiece comprises a pistol-shaped housing including a forward/rearward extending barrel and a handle fixedly depending from the barrel. A motor and control circuit are supported in the barrel. The motor drives a tool carrier at the front end of the barrel. In one preferred embodiment, the housing is of formed sheet metal and the motor, control unit and a drive train for driving the tool carrier, are mounted as a sealed unitary cartridge within the sheet metal barrel. In one embodiment, the battery is inserted upward into the bottom of the handle and telescopes therein for a substantial distance to permit a relatively compact handle arrangement while yet permitting a full size handle rigidly joined to the barrel of the housing.

22 Claims, 9 Drawing Sheets

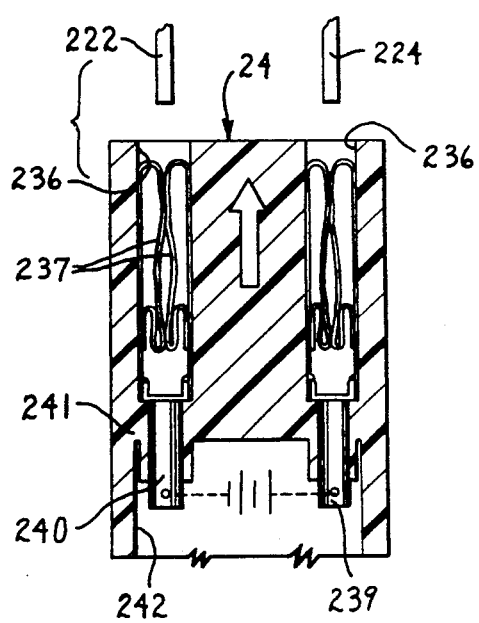
FIG.15
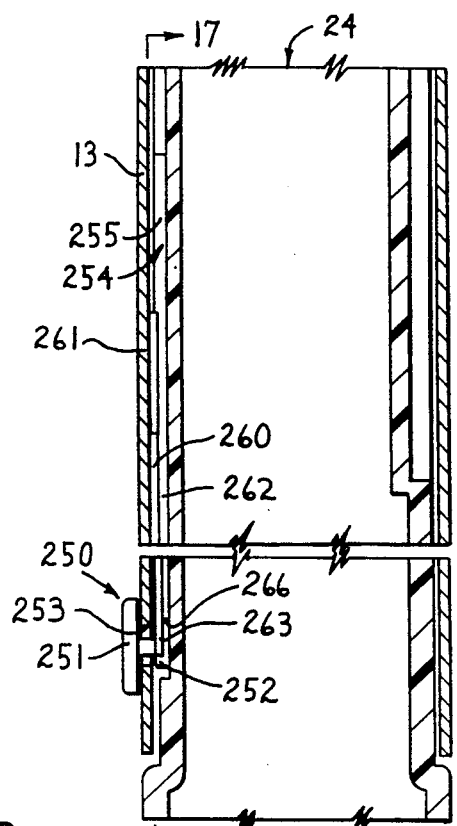
FIG.16
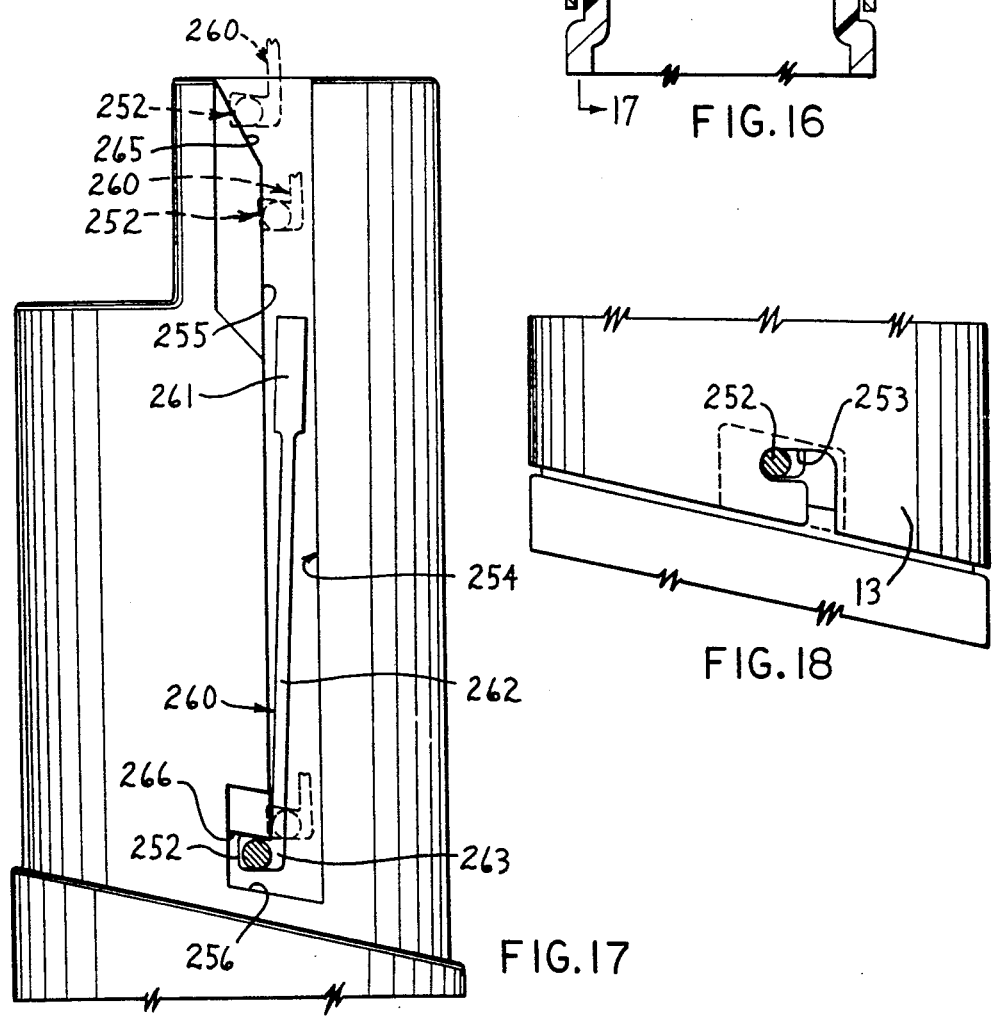
FIG.17
FIG.18

5,207,697

BATTERY POWERED SURGICAL HANDPIECE

FIELD OF THE INVENTION

This invention relates to a battery powered surgical handpiece.

BACKGROUND OF THE INVENTION

Battery powered surgical handpieces have been commercially available for some time and have been found convenient by surgeons for reasons including the lack of a trailing power cord. A typical handpiece has a pistol shaped housing including a barrel and depending handle, a trigger at the juncture of the handle and barrel for turning on and off and setting the speed of an internal motor, and a tool carrier or chuck at the front end of the barrel. Typically, a housing incorporates the handle and barrel and contains a removable, rechargeable battery, a motor and a drive train connecting the motor and tool carrier. Handpieces of this general kind have been equipped as rotary drills, reamers, wire drivers, and saws of sagittal, oscillating and reciprocating type, for example.

Battery operated surgical handpieces of this kind have been marketed by the assignee of the present invention, Stryker Corporation of Kalamazoo, Mich., including for example the model No. 2102. In these, the housing has been formed of a gracefully contoured sheet metal envelope of pistol contour, typically a stainless steel envelope, sized to comfortably fit the hand of the user. By locating the motor and speed reduction gearing in the handle, to drive through angled gearing the output shaft extending forward in the barrel, and inserting the rechargeable battery pack removably into the open rear end of the barrel, and providing a hole axially through the battery pack in coaxial alignment with a suitable through hole in the output shaft, it has been possible to provide a wire driver type surgical handpiece, namely one in which a wire inserted through the rear end of the barrel is fed out the forward end of the barrel to a surgical site as part of a drilling operation for example.

A further example of battery powered surgical handpieces of this general kind is disclosed in Mongeon et al U.S. Pat. No. 4,728,876. Same comprises a housing having a barrel of circular cross section and a detachable handle releasably dependent therefrom. The trigger is mounted pendently from the barrel and is thus separable from the handle. The handle carries a rechargeable battery and switch means actuable by the trigger, being coupled thereto in a releasable manner to permit ready removal of the handle in a manner to allow charging/replacement of the battery handle. Rearward sliding of the handle with respect to the barrel achieves release. A cylindrical rear portion of the barrel is rotatable about the central axis of the barrel to achieve forward/off/reverse control of the motor and houses the brushes and commutator portion of the motor. Extending forward along the barrel are the motor, a two-speed shiftable gear reduction set, and an output shaft for driving a tool carrier.

The present invention arose from a continuing effort to improve battery powered surgical handpieces of the general kind exemplified above.

Accordingly, embodiments of the present invention are respectively intended to fulfill one or more of the following objects and purposes. A battery powered surgical handpiece is well balanced and has a contoured rigid sheet metal housing fitted to the human hand to maximize comfort and controllability in surgical procedures of substantial duration. A motor control circuit, motor, speed reduction gearing, output shaft and tool carrier can be preassembled in a cartridge and test run prior to insertion in the housing barrel, so that if any part of such cartridge is defective, it will be discovered and can be cured prior to completing assembly of the handpiece. The motor, drive train and output shaft are precisely coaxially located in a precisely configured, circular cross section cartridge casing, which in turn is fixedly though removably located in the formed sheet metal barrel, so as to avoid the substantial difficulty (if not impossibility) of forming the sheet metal barrel as precisely as needed for proper location of the motor and speed reduction unit and output shaft with respect to each other while permitting the above-mentioned comfortable fitting of the housing, including the barrel, to the human hand. The exteriors of the motor, speed reduction unit and output shaft need not be individually sealed, fitted or fixed to the inner surface of the sheet metal housing, and the barrel and handle can be of non-circular cross section. Adequate room is provided for a powerful motor without need for a handle cross section which is too large or improperly shaped for maximum use or comfort and control. The motor is of brushless type having a permanent magnet rotor. The electronic circuitry for controlling the brushless DC motor, in response to trigger and reversing switch actuation, is contained in the rear portion of the barrel immediately behind the brushless DC motor. A central passage opens through the front and rear ends of the barrel and extends through the electronic control unit in coaxial relation with corresponding central passages through the motor, speed reduction unit and output shaft, to enable use of the handpiece as a wire driver. Seals prevent foreign material and moisture (e.g. steam in a sterilizing autoclave) in the central passage from entering into the interior of the housing and into components within the housing and outside of such central passage. Adjacent the rear of the motor, a rear seal is disposed between fixed and rotating parts of the drive train but is not required to engage the relatively high speed motor shaft, so as to substantially extend the expected operating life of such seal and minimize power loss in the seals. The output shaft has a heavy duty forward portion capable of transmitting substantial torque to a tool carrier and a much lighter duty rear portion extending loosely through and rearward of the motor for rotatably engaging a rear seal, the heavy front and light rear portions of the output shaft being rigidly fixed to and sealed with respect to each other, the two parts of the output shaft being hollow and telescoped and yet sealed at their joinder to prevent ingress of moisture into the barrel of the handpiece. The trigger actuates a variable speed control and a separate on/off switch structure so that actuating movement of the trigger first must close the switch contacts to their "on" position, prior to raising the speed to control portion of the trigger unit above a zero speed setting. Use of a brushless permanent magnet motor eliminates reliability and maintenance problems associated with brushes and provides greater operating efficiency of the motor thereby allowing greater run time for a given battery capacity, and thereby permitting a reduction in battery size for a given run time, to reduce the weight and bulk of the handpiece. The upper portion and major length of the handle connects rigidly and permanently and indeed integrally with the barrel of the handpiece housing to provide a rigid, long lasting handpiece exterior not readily damaged and particularly wherein the handle cannot come loose from the barrel in use. The trigger is mounted on this fixed portion of the handle. From the bottom portion of the handle protrudes a minor portion of a rigid battery which has a major upper portion insertable upward into the open bottom of the handle, such that the exposed part of the battery acts simply as a downward extension of the handle, thereby not interfering with the fit of the hand of the user to the handpiece or with the balance of the hand-piece, and permitting use of battery packs of greater length where greater battery capacity is needed, and allowing substantial overlap of the battery telescoped within the handle for rigidity of mounting of the battery pack with respect to the handle, and providing more than adequate space for latching and electrical contact of the battery pack with respect to the rest of the handpiece. The substantially telescoped overlap of the battery pack and a latch mechanism within the hollow bottom portion of the handle substantially eliminates any tendency for handpiece vibration or careless handling to loosen or break the battery pack/handpiece connection.

Further objects and purposes of the invention will be apparent to persons acquainted with apparatus of this type upon reading the following description and inspecting the accompanying drawings.

BRIEF DESCRIPTION OF THE DRAWINGS

FIG. 7A is a fragmentary rear view of the back cap on the barrel of the housing of FIG. 2, showing the forward/off/reverse switch manual actuator.

FIG. 7B is a fragmentary sectional view substantially taken on the line 7B—7B of FIG. 7A.

FIG. 12A is a graphical comparison of the motor speed/trigger displacement relationship of the trigger unit of FIG. 7.

FIG. 15 is a fragmentary sectional view substantially taken on the line 15—15 of FIG. 11.

FIG. 16 is a fragmentary sectional view substantially taken on the line 16—16 of FIG. 11.

FIG. 17 is a sectional view substantially taken on the line 17—17 of FIG. 16 and showing the left side (looking forward) of the battery pack, namely the side of the battery pack opposite that shown in FIG. 7.

FIG. 18 is a fragment of the bottom portion of the housing handle taken from the left side thereof, namely opposite the side thereof shown in FIG. 1.

SUMMARY OF THE INVENTION

A pistol-shaped surgical handpiece comprises a pistol-shaped housing including a forward/rearward extending barrel and a handle fixedly depending from the barrel. A motor and control circuit are supported in the barrel. The motor drives a tool carrier at the front end of the barrel. In one preferred embodiment, the housing is of formed sheet metal and the motor, control unit and a drive train for driving the tool carrier, are mounted as a sealed unitary cartridge within the sheet metal barrel. In one embodiment, the battery is inserted upward into the bottom of the handle and telescopes therein for a substantial distance to permit a relatively compact handle arrangement while yet permitting a full size handle rigidly joined to the barrel of the housing.

DETAILED DESCRIPTION

Figure 1:
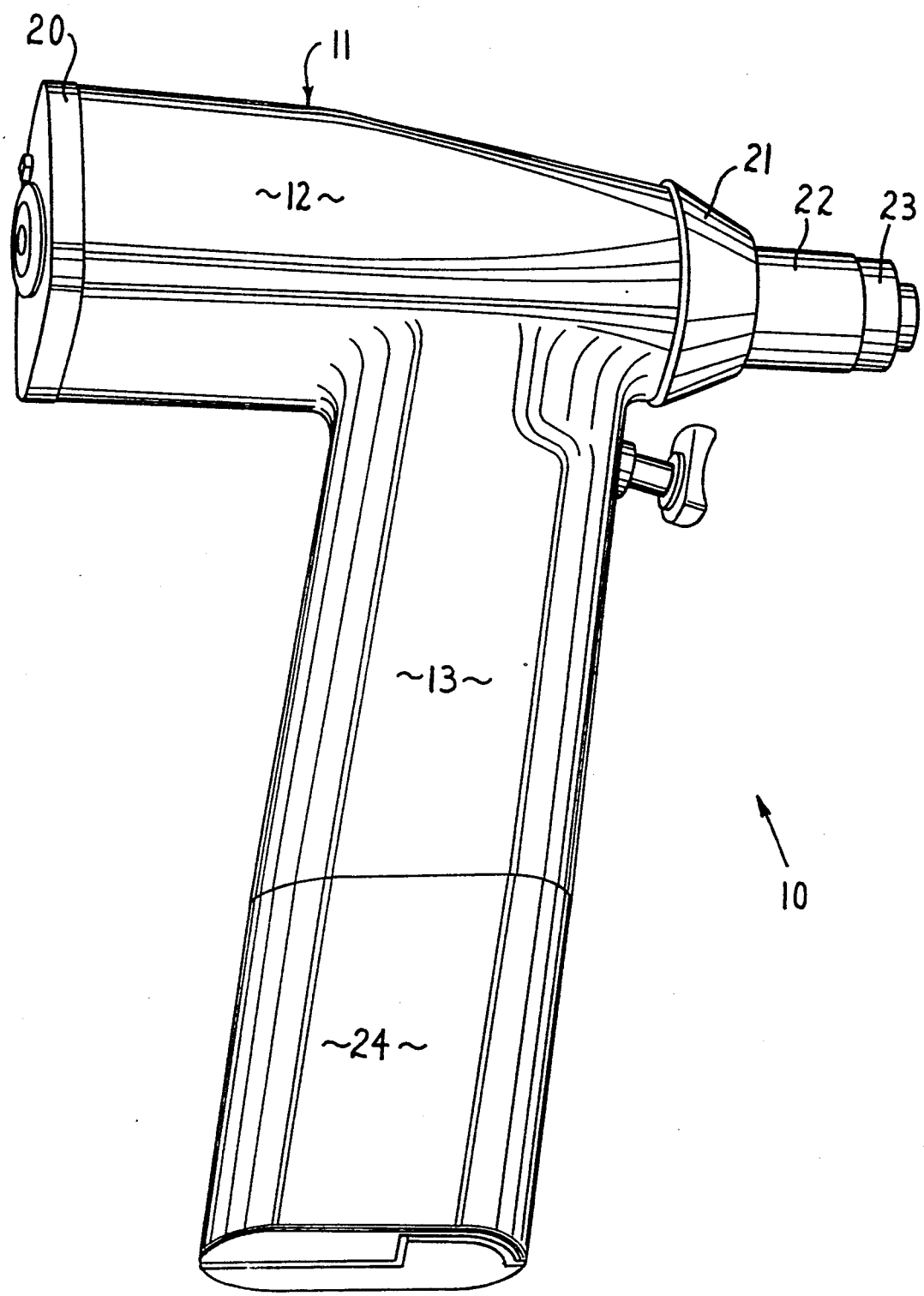
FIG. 1 is a pictorial view of the handpiece embodying the invention.

A surgical handpiece 10 (FIG. 1), embodying the invention, comprises a sheet metal housing 11 including a forward/rearward extending barrel 12 from a central portion of which depends a handle 13 slightly swept back at a small angle to the perpendicular. The barrel and handle are configured for comfortable gripping by human hands of a variety of sizes. The housing 11 comprises a rigid but thin sheet metal skin which is also aesthetically pleasing to view. The barrel 12 behind the handle 13 is of substantially square cross section, seen in FIG. 1, with rounded corner edges and in the area above the handle 13 transitions in shape to a generally frusto-conical configuration extending a short distance ahead of the handle 13. A back cap 20 fixedly closes the generally square rear end of the barrel 12. A front nose cone 21 fixedly closes the front end of the barrel 12 and has a central opening through which protrudes the exposed front portion 22 of the outer shell of a motor-drive train-output shaft containing cartridge hereafter discussed. A tool carrier 23 extends beyond the front portion 22. Handpieces of the general type shown at 10 may be adapted to support and drive tool carriers of a variety of alternative kinds, for example carriers or chucks for drills, reamers, wire drivers, and sagittal, oscillating or reciprocating saws, to name several. In the embodiment shown, for the sake of example, the handpiece 10 is shown as a drill capable of wire driving use.

The bottom of the handle 13 is open and receives the upper end of a battery pack 24 (FIG. 7) in snugly telescoped relation upwardly therein. In the embodiment shown, the upper part 25 of the battery pack 24 extends substantially the full height of the handle 13 so as to be firmly sheathed in the handle 13. The bottom part 26 of the battery pack 24 extends below the bottom of the handle 13 and is circumferentially enlarged from the inside dimension of the handle 13 to the outside dimension thereof, to form a step 27 opposing the bottom edge of the handle 13 and so that the outside of the bottom portion 26 of the battery pack 24 forms a smooth continuation downward of the handle 13.

A trigger unit 30 comprises a trigger mechanism 31 (FIG. 7) disposed within the upper front part of the handle 13. A trigger shaft 32 protrudes forward from the trigger mechanism 31 through a hole in the front face of the handle 13, where it is retained by an annular externally threaded keeper 33. A trigger member 34 is fixed on the exposed forward end of the trigger shaft 32 and is contoured for comfortable squeezing by the finger of the user. In the embodiment shown, the top front corner portion of the battery pack 24 is notched at 35 to leave room for the trigger mechanism 31.

Removably disposed in the barrel 12 is a cartridge 40 (FIG. 2) having a circular cross section casing providing a rigid, precisely machined container for a drive train generally indicated at 42 which drives the tool carrier 23. The cartridge casing 41 includes a rear cylindrical motor support shell 43 fixedly sleeved at its front end over the rear portion of a front, stepped output shaft support shell 44. The shells 43 and 44 are fixed together by any convenient means, here one or more radial pins 45. An annular seal (here an O-ring) 46 radially interposed between the shells 43 and 44 prevents fluid leakage therebetween into the casing 41. The front end of the sleeve 43 is precisely axially located against a radial flange 47 on the sleeve 44.

An annular spacer sleeve 48 is axially trapped between a front facing step 50 on the front shell 44 and the rear end of the nose cone 21. The spacer sleeve 48 is fixedly supported within the front end of the barrel 12 by a front, radially outwardly extending flange 51, which is an integral part of the spacer sleeve 48 and is fixed, as by welding, inside the front end extremity of the skin of the barrel 12. The stepped front shell 44 has rear, mid and front portions, indicated at 52, 53 and 22 respectively, the front portion 22 of the front shell 44 defining the aforementioned front portion of the overall structure of the barrel 12. The front shell portions 52, 53 and 22 are of progressively lesser diameter. The mid portion 53 is snugly but axially slidably supported in the spacer sleeve 48. The mid portion 53 has external threads 54 at its front end and on which the nut-like nose cone 21 is threadedly received, to abut the front ends of the barrel 12 and spacer sleeve 48. The front portion 22 of the front shell 44 extends snugly out through the central opening of the front end of the nose cone 21.

A rear plug 60 snugly inserts in the open rear end of the rear shell 43. An O-ring 61 radially seals between the rear plug 60 and overlying portion of the rear shell 43. A radially outward flange 62 on the rear end of the plug 60 axially loosely opposes a lesser diameter radially outwardly extending flange 63 on the rear end of the rear shell 43 and extends radially outward therebeyond. A sleeve-like retaining nut 64 has at its forward end a radially inward extending annular flange 65 which snugly but slidably surrounds the intermediate portion of the rear shell 43 and abuts the front edge of the flange 63 of the rear shell 43 to prevent the retaining nut 64 from sliding rearward off the rear shell 43. The rear portion of the retaining nut 64 threadedly surrounds the flange 62 of the rear plug 60 and upon tightening pulls the rear plug 60 into the rear shell 43 until it hits a stop, namely the rear end of the stator of a conventional brushless DC motor 70, a portion of the rotor of which is shown at 71. The stator 72 of the motor 70 surrounds the permanent magnet rotor 71 in a conventional manner which needs no description here. The motor 71 fits radially loosely within the rear shell 43 and is axially fixed therein by being axially pressed between the rear plug 60 and an intermediate baffle 73. The baffle 73 fits snugly within the rear shell 43 and abuts a rear facing step on the interior surface of the rear shell 43 so as to positively prevent forward shifting of the baffle 73 within the rear shell 43. Hence, the stator 72, and hence the motor 70 as a whole, is positively axially located in the rear shell 43 by compression axially between the rear plug 60 and the baffle 73.

A tubular high speed motor shaft 75 is fixedly surrounded by and coaxially supports the motor rotor 71 and extends forwardly and rearwardly therebeyond. Front and rear bearings 76 and 77 are fixed within the central openings of the baffle 73 and rear plug 60 and are axially fixed on the tubular motor shaft 75 in front of and behind the rotor 71 to rotatably support such shaft and rotor. The front bearing 76 is preferably a press fit in the baffle 73 and the rear bearing 77 may be located in the rear plug 60 by a spacer 78 and other structure hereafter discussed located therebehind. The rotor 71 and hence shaft 75 are precisely axially located between the front and rear bearings 76 and 77 by front and rear spacers 81 and 82.

Front and rear output shaft bearings 83 and 84 are fixed within the front shell 44. The bearings 83 and 84 are here of low friction (such as ball) type. The front bearing here is press fitted in the front portion 22 of front shell 44 and the rear bearing 84 is here retained by a snap ring 85 against rearward movement out of the front shell 44. The bearings 83 and 84 are precisely axially separated by a slightly stepped-in portion 86 of the central bore 87 of the front shell 44.

A low speed output shaft 90, of substantially heavier wall thickness than the high speed motor shaft 75, is rotatably supported within the bearings 83 and 84 and extends lengthwise beyond the front and rear ends of the rear shell 53. The output shaft 90 is axially located in any convenient way, as by a snap ring 88 and a carrier 110 hereafter described which straddle the bearing 84 which in turn is fixed axially within the housing by the step 86 and the snap ring 85. It will be understood that the low friction bearings 76 and 77 and 83 and 84 are conventional and thus have radially inner and outer races (not shown) separated by low friction elements such as balls (not shown), wherein the inner and outer races can be fixed to the fixed structure above described and the inner races can be fixed to the respective shafts 75 and 90.

An annular seal unit 91 of conventional type is interposed radially between the front portion 22 of the front shell 44 and the output shaft 90 to effect a fluid seal therebetween, to prevent leakage of moisture from outside the housing 11 rearwardly into the cartridge casing 41. The seal 91 may be fixed by any convenient means, such as a press fit, within the front shell 44.

The tool carrier 23 is here in the form of a conventional rotary chuck, and more particularly of the kind which is axially rearwardly displaceable to enable insertion of a tool therein, the tool being retained by balls 92 and the chuck being forward biased by a compression spring 93 rearwardly backed by a snap ring/washer set 94 fixed on the output shaft 90 adjacent its front end.

A speed reducer unit 100, here in the form of a two-stage planetary gear set, drives the output shaft 90 at a reduced speed from the motor shaft 75. The speed reducer unit 100 is here a double planetary unit. An annular first planet carrier 101 is disposed just in front of the motor shaft 75 and fixedly supports three evenly circumferentially spaced rearward extending planet shafts 102. Three identical planet gears 103 are rotatable in axially fixed relation on the respective planet shafts 102. The planet gears 103 mesh with a sun gear 104 fixed on the forward end of the motor shaft 75 and with a surrounding annular ring gear 105 fixed on the interior wall of the rear shell 43. Thus, rotation of the motor shaft 75 causes the planet gears 104 to walk circumferentially along the ring gear 105 and thereby orbit the planet shafts 102 and rotate the first annular carrier 101 at a slower speed than the motor shaft 75.

The speed reducer 100 further includes a second carrier 110 located just rearward of the output shaft 90. A plurality, here three, of evenly circumferentially spaced planet shafts 111 are fixed to and extend rearward from the second carrier 110 and rotatably support planet gears 112 which are axially fixed thereon. The planet gears 112 mesh with a second sun gear 113 coaxially fixed on and constituting a tubular front extension of the first carrier 101. The planet gears 112 further mesh with the surrounding annular ring gear 105. Accordingly, rotation of the second carrier 110 causes the planet gears 112 to walk circumferentially along the ring gear 105 and thus orbit the planet shafts 111 and rotate the second carrier 110 at a speed slower than the rotational speed of the first carrier 101 and hence the rotational speed substantially less than that of the motor shaft 75. The second carrier 110 has a front extending flange which snugly surrounds the rear end of the output shaft 90 and rotatably drives same through any convenient positive means, here a key 114. Thus, the output shaft 90 is rotatably driven by the motor shaft 75 at a speed substantially less than that of the motor shaft 75.

Figure 2:
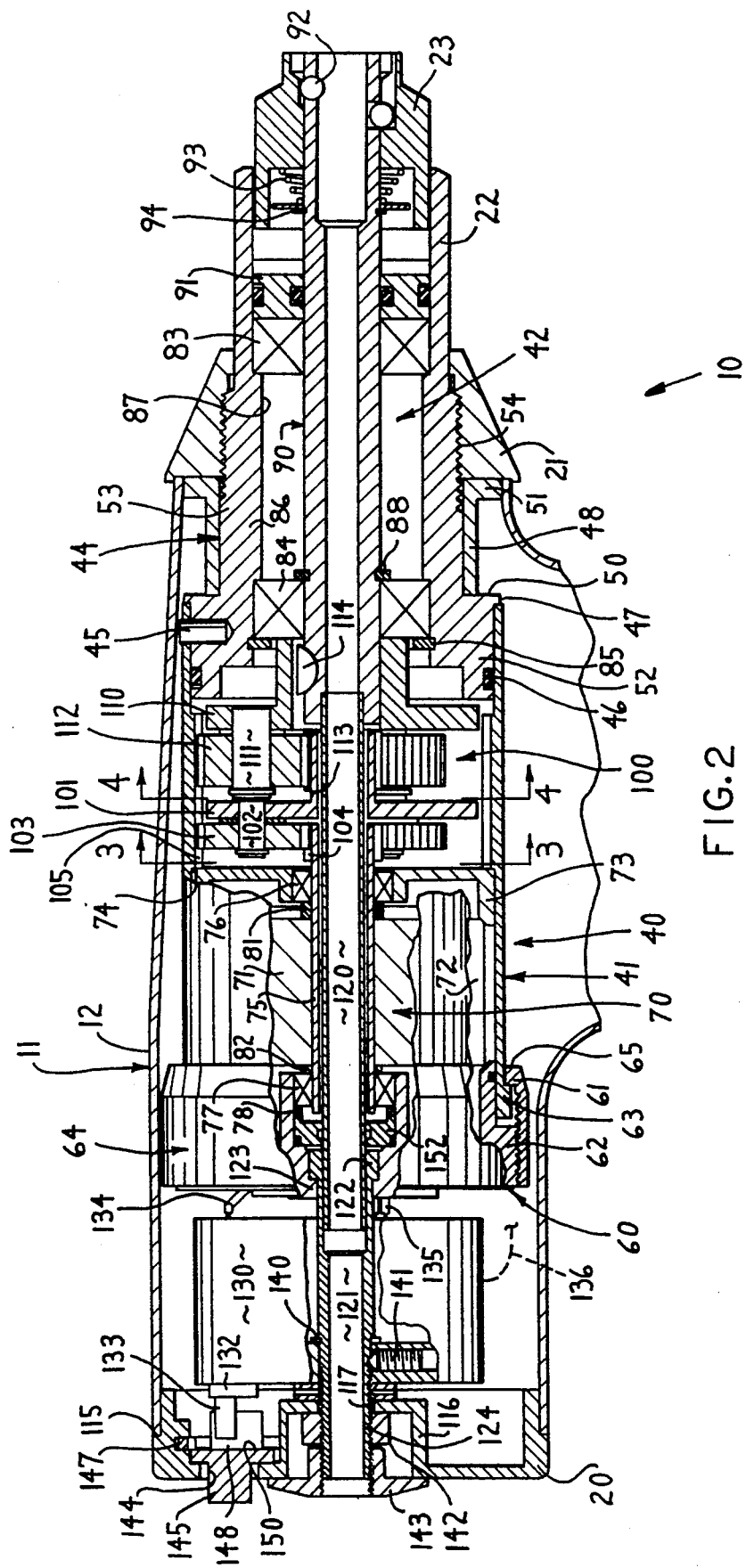
FIG. 2 is a fragmentary elevational view partially broken away in central cross section, of the barrel of the handpiece of FIG. 1.
Figure 3:
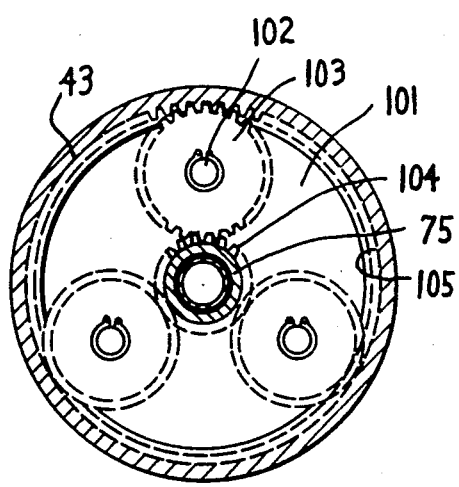
FIG. 3 is a cross sectional view substantially taken on the line 3—3 of FIG. 2.
Figure 4:
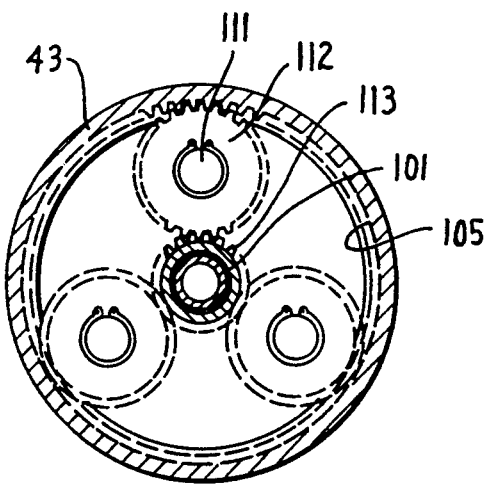
FIG. 4 is a sectional view substantially taken on the line 4—4 of FIG. 2.

The rear end of the barrel 12 is closed by the above-mentioned back cap 20 (FIG. 2). The periphery of the back cap 20 is stepped at 115, the forward portion of the back cap being snugly and fixedly telescoped into the open rear end of the barrel 12 while the rear portion of the back cap abuts the rear end of the barrel 12. The back cap 20 may be held fixedly in place to close the rear end of the barrel by any convenient means, such as fastening with a nut 142 hereafter discussed. The central portion of the back cap 20 is stepped forward to form a rearward opening central cup 116 having a central hole 117 therethrough.

The output shaft 90 has a thin walled, tubular, rearward extension 120 (FIG. 2) coaxially fixed thereto for rotation therewith. In the embodiment shown, the front end of the rearward extension 120 is telescoped a short distance in and fixed, by any convenient means, such as laser welding, to the end of the output shaft 90. The output shaft extension 120 extends loosely coaxially through the annular first carrier 101, the tubular motor shaft 75, and rearward beyond the rear plug 60 of the cartridge 40 and hence to the rear of the cartridge 40 itself.

A fixed tube 121 is loosely sleeved over the rear shaft extension 120 in coaxial relation therewith. The tube 121 includes a radially outward protruding flange 122 at the front end thereof. The annular flange 122 is received in the rear plug 60 and is welded to a radially inward extending flange 123 of the rear plug 60. The tube 121 extends rearward out through the central opening 117 in the back cap 20. The rear end portion of the tube 121 is threaded at 124.

Figure 7:
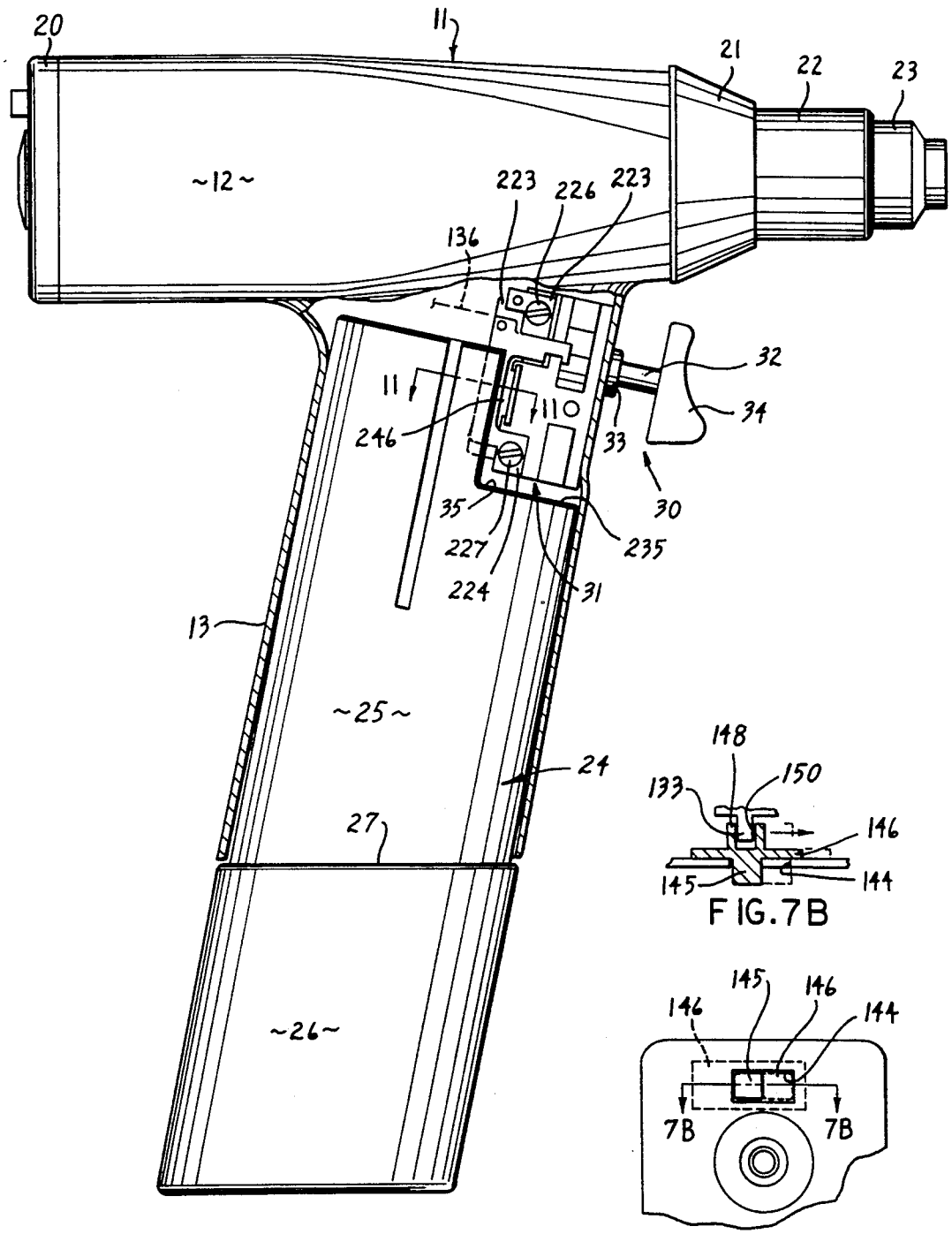
FIG. 7 is a right side elevational view of the handpiece of FIG. 1 with the handle broken away in central section to show the trigger unit and an inserted battery pack.

A motor control unit 130 is here schematically shown as a generalized block of annular form. The motor control unit 130 includes circuitry for controlling on/off, motor speed, and forward/reverse rotation direction of the motor 70 and such circuitry may be of any conventional type. If desired, the motor control unit 130 may incorporate a circuit similar to that used in aforementioned Model 2102 available from the assignee of the present invention. However, in one unit constructed in accord with the invention, the circuitry of the motor control unit 130 was of the kind shown in U.S. Pat. No. 5,136,220, assigned to the assignee of the present invention. In the embodiment shown, the motor control unit 130 incorporates a forward/off/reverse switch schematically shown at 132, having a laterally shiftable actuator finger 133 extending rearward from the motor control unit 130. The motor control unit 130 controls the on/off, forward/reverse, and speed functions of the motor by suitable electrical connections therewith, several being shown at 134 and 135. The motor control unit 130 also has electrical connections to the trigger unit 30 as schematically indicated by the broken line 136 (FIGS. 2 and 7).

Forward displacement of the motor control unit 130 along the rear tube 121 is positively blocked by a suitable abutment, here a snap ring 140 (FIG. 2). The control unit 130 is maintained snugly against the snap ring 140 by set screws 141.

A nut 142 threads on to the threaded rear end portion 124 of the tube 121 and is tightened against the forward end wall of the cup 116 to hold on the back cap 20. The nut-like nose cone 21, when tightened, axially presses together the nose cone 54 and the spacer sleeve 48 which is welded to the front end of the barrel 12, which keeps the cartridge axially fixed in the barrel 12. A removable annular decorative cap 143 is removably fixed on the rim portion of the rear tube 121 behind the nut 142 by a sliding friction fit or, in the embodiment shown, by threading thereon.

The back cap 20 has, above the decorative cap 143, a horizontally extending slot 144 (FIGS. 2, 7a and 7b) in which is horizontally slidable a thumb actuable slider button 145. The slider button 145 at the axial mid portion thereof has a radially outwardly extending perimeter flange 146 which interferes with the portion of the back cap surrounding the slot 144 and prevents the slider button 145 from escaping rearward out of the back cap 20. In the preferred embodiment shown, a keeper 147 (FIG. 2) fixed within the back cap 20 prevents the slider button 145 from shifting forwardly but allows horizontal sliding of the slider button 145. The slider button 145 has a forward portion 148, which extends forwardly beyond the flange 146 and defines a forwardly and vertically opening slot 150 (FIG. 7b) in which the switch finger 133 is snugly but forwardly slidably received. Thus, manual shifting of the slider button 145 horizontally correspondingly horizontally shifts the switch actuator finger 133 to shift the switch 132 between its forward/off/reverse positions for requesting corresponding rotational modes of the motor rotor 71.

Figure 5:
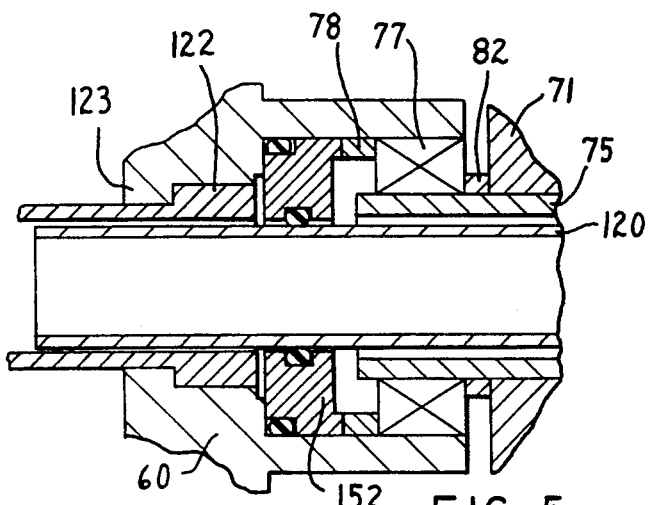
FIG. 5 is an enlarged fragment of FIG. 2 showing the rear shaft seal.

An annular rear seal unit 152 is fixed snugly within the central opening of the rear plug 60, as seen in FIGS. 2 and 5, and surrounds, in sealing relation therewith, the rear extension 120 of the output shaft. The rear seal unit 152 is disposed axially between the rear tube 121 and motor shaft 75, in spaced relation from both. While contaminating fluids (for example steam in an autoclave, liquid from the surgical wound during surgery, etc.) can enter the central cannula defined within the output shaft 90, output shaft extension 120 and fixed rear tube 121, the rear seal unit 152 blocks such fluid as may enter the radial space between the telescoped rear tube 121 and rear output shaft extension 120, from entering past the rear motor shaft bearing 77 into the interior eccentric spaces of the cartridge 40. Since the rear seal unit 152 bears on the relatively slowly rotating rear extension 120 of the output shaft, it is subjected to substantially less wear and has a substantially longer life than would be the case if it were instead sealing against the relatively high speed motor shaft 75 and it produces less energy losses, thus extending run time of the battery.

Figure 6:
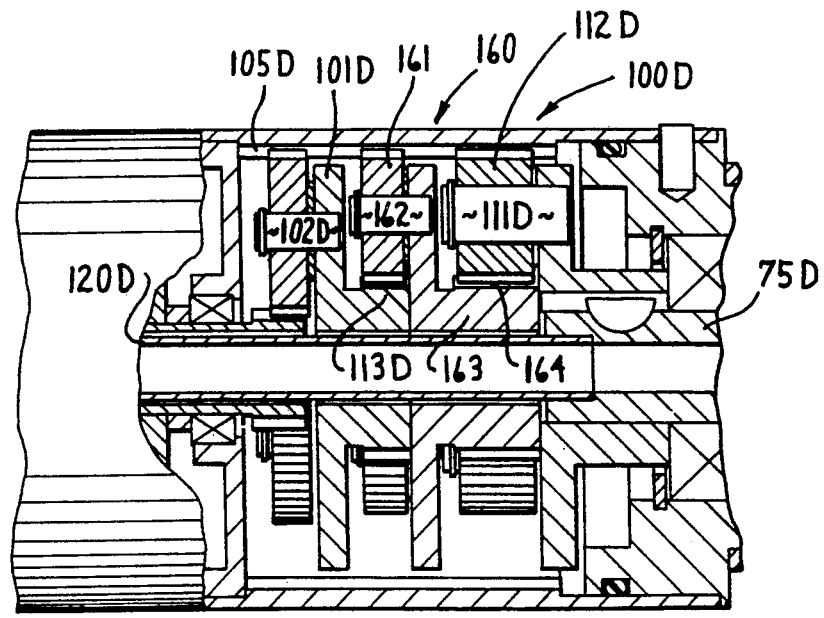
FIG. 6 is an enlarged fragment of FIG. 2 showing a modified speed reduction unit.

FIG. 6 discloses a modified speed reducer unit 100D. Structural elements similar to structural elements in the FIG. 2 embodiment carry the same reference numerals, with the suffix D added thereto, in the FIG. 6 modification. The modified speed reducer unit 100D is similar to the unit 100 above described but has an extra planetary set operatively interposed between the first, or rear, carrier 101D and a front set of planet gears 112D. Such extra planetary set is generally indicated at 160 (FIG. 6) and comprises a third set of planet gears 161 evenly and circumferentially spaced about and meshing with an intermediate sun gear 113D for circumferentially walking along a ring gear 105D. The planet gears 161 are rotatably supported on planet shafts 162 in turn extended rearward from and evenly circumferentially fixed on a forward intermediate carrier 163 in turn carrying a sun gear 164 driving output planet gears 112D.

The extra planetary set 160 reduces the rotational speed of the output shaft 75D by supplying an extra speed reduction ratio, such that the FIG. 6 embodiment may be used, for example, for a reamer type handpiece, whereas the FIG. 2 structure above described may be used for a drill type handpiece in which higher output speed is required.

Figures 8, 12:
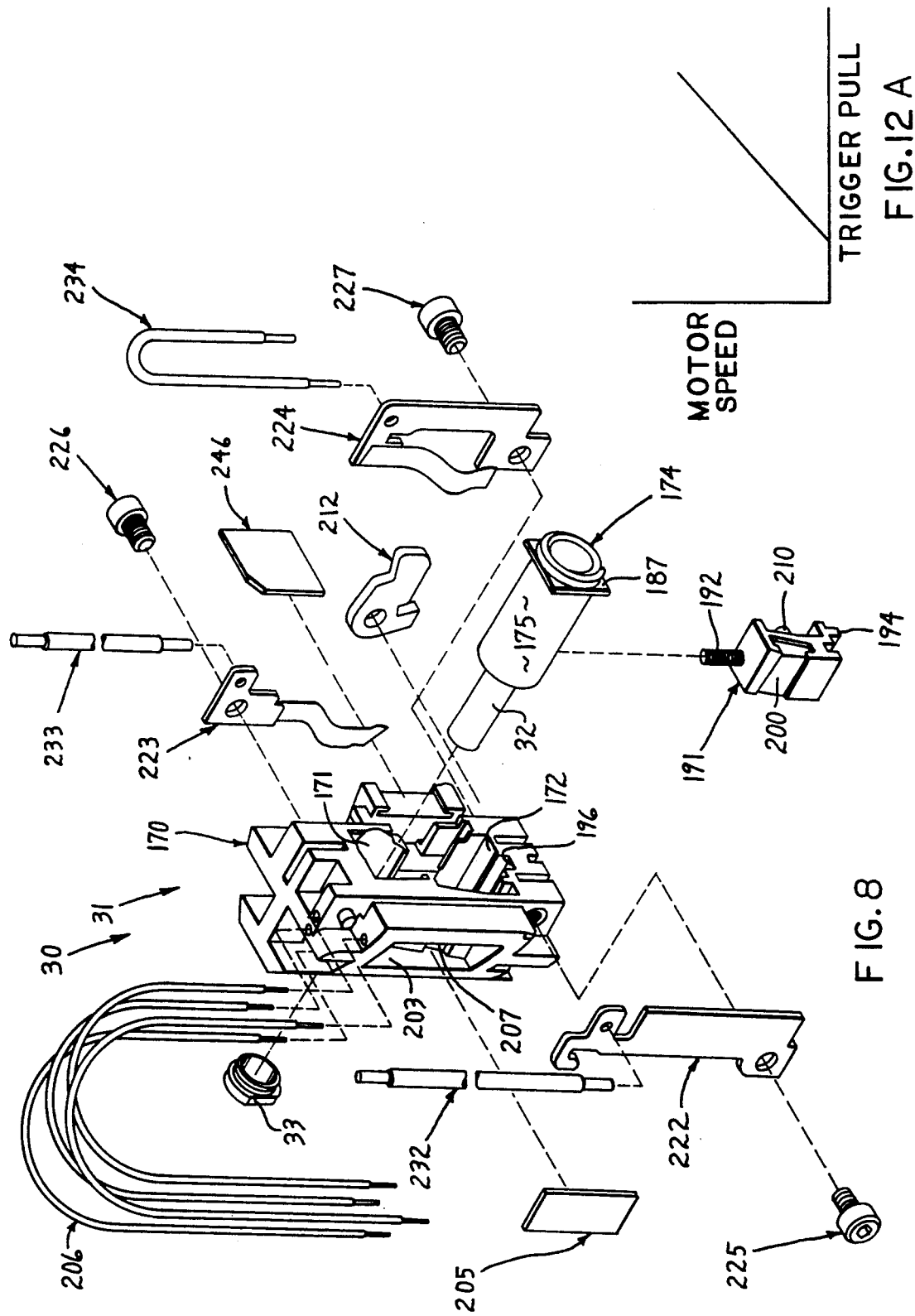
FIG. 8 is an exploded pictorial view of the trigger unit of FIG. 7, excluding the trigger member.
FIG. 12 is a cross sectional view substantially taken on the line 12—12 of FIG. 9.
Figure 9:
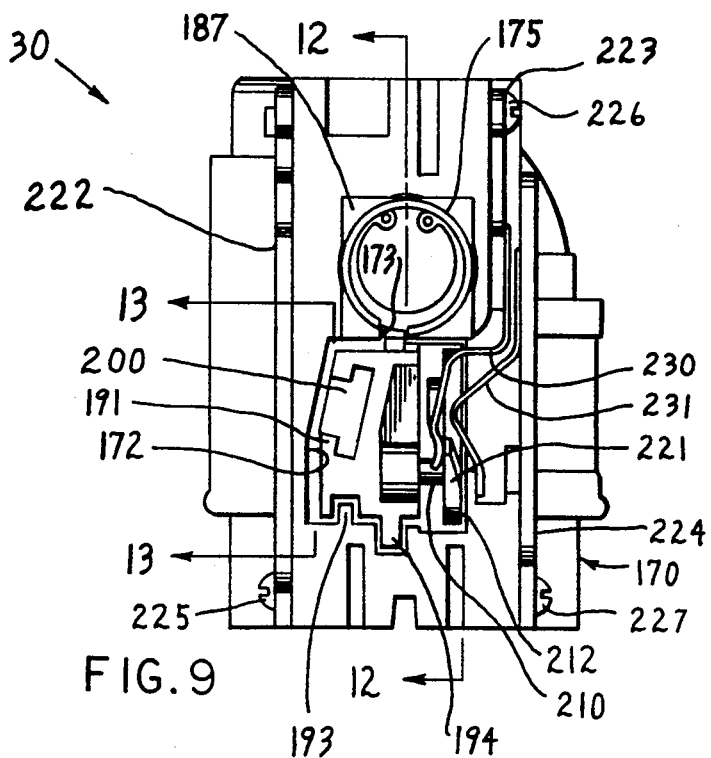
FIG. 9 is an enlarged rear view, looking from the left in FIG. 7, of the trigger unit thereof.
Figure 10:
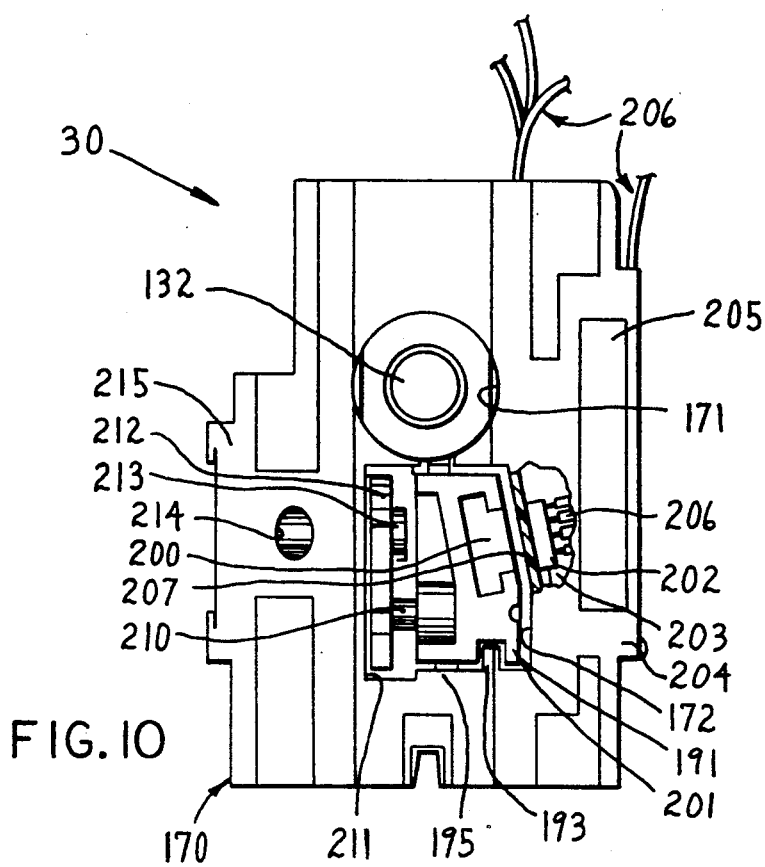
FIG. 10 is a partially broken front elevational view of the trigger unit of FIG. 9.
Figure 12:
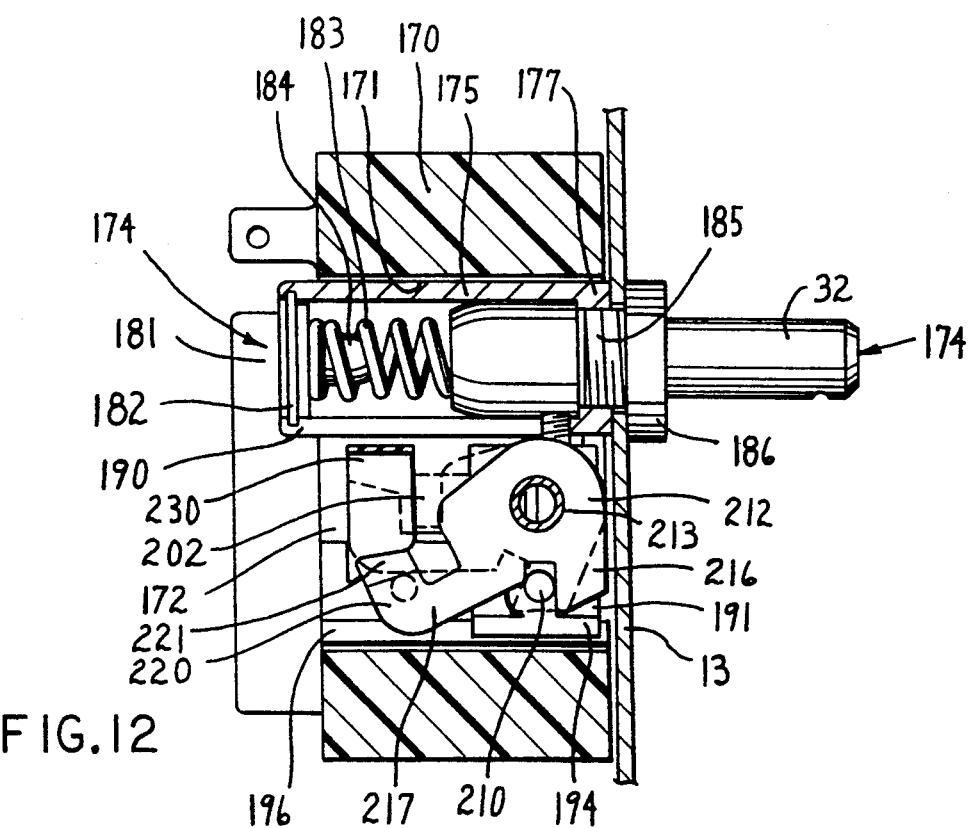

Turning to FIGS. 8-12, the trigger unit 30 comprises a support block 170 which is rigid and is preferably of molded, electrically insulative, plastics material. The block 170 tapers forwardly as seen from the top in FIG. 11. Top and bottom through holes 171 and 172 extend forwardly/rearwardly through the block 170. The top through hole 171 is substantially circular in cross section and of substantially constant radius throughout its length. The bottom through hole 172, as seen for example in FIG. 10, is generally rectangular in shape though with deviations in shape in its bottom wall and one side wall as hereafter discussed. A slot 173 (FIG. 9) communicates between the top and bottom through holes and runs the forward/rearward depth of the block 170. The slot extends parallel to the longitudinal axes of the top and bottom through holes 171 and 172.

The trigger shaft 32 is part of a plunger assembly 174 (FIG. 12) which further comprises a cylinder 165 which is received snugly in and extends forward/rearward through the top through hole 171 into the block 170. The trigger shaft extends forward out of the cylinder 175. The rear end of the trigger shaft 32 comprises a radially enlarged head 176 which is snugly slidable axially in the cylinder 175 and is retained at its forward end therein by a radially inward extending flange 177 at the front end of the cylinder 175. The rear end of the cylinder 175 is closed by a stopper plate 181 held in place by a snap ring 182. A coil compression spring 183, backed by the stopper plate 181, presses forward on the head 176 of the trigger shaft 32 to push same forward and into its forward position shown. A pin 184 centrally fixed to the stopper plate 181 extends forward therefrom for a short distance, and telescopes into the rear end portion of the coil spring 183 to locate same centrally within the cylinder 170. An externally threaded collar 185 extends loosely through a hole in the front wall of the handle 13 and threads into the annular flange 177 at the front end of the cylinder 175 to tightly sandwich the skin of the handle 13 between the front end flange 177 of the cylinder and a front radial flange 186 of the collar 185.

The cylinder 175 has an external radial flange 187 (FIGS. 8 and 9). The flange 187 is here square in shape and is disposed near but not at the rear end of the cylinder 175. Such square flange 187 provides diagonally opposed corner portions extending radially outward from the outer peripheral surface of the cylinder 175. The block 170 and front skin of the handle 13 are tightly axially gripped between the flange 186 on the threaded front collar 185, on the one hand, and the square flange 187 of the cylinder 175, on the other hand. In this way, the block 170 is firmly but releasably held against the inside of the front part of the handle 113. The bottom periphery of the cylinder 175 has an axially extended slot 190 extending almost the entire length of the cylinder and communicating with the slot 173 which communicates vertically between the top and bottom through holes 171 and 172 of the block 170.

The bottom through hole 172 has a block-like carrier 191 (FIGS. 9 and 10) disposed for front/rear sliding movement therein. The carrier 191 occupies the left side of the bottom through hole 172 as seen looking forwardly as in FIG. 9.

A threaded stud 192, fixedly upstanding from the top of the carrier 191, extends up through the slot 173 (FIG. 9) in the block 170 and the slot 190 in the bottom of the cylinder 175 and is threadedly engaged in the bottom of the head 176 of the plunger shaft 32. Accordingly, forward/rearward movement of the plunger shaft 32 and head 176 by the user carries the carrier 191 through corresponding forward/rearward movement. A tongue 193 of the block 170 is upstanding in the bottom through hole 172 in such block and is received in a corresponding downward opening groove in the bottom of the carrier 191, as seen in FIG. 9, such tongue 193 and corresponding groove being aligned in the forward/rearward direction to help guide the forward/rearward movement of the carrier 191.

A depending tongue 194 on the bottom of the carrier 191 is slidably received in a corresponding upward opening groove 196 (FIG. 12) in the bottom of the bottom through hole 172 in the block 170. The front end of the groove 196 is closed, as seen at 195 in FIG. 10, to positively preclude the carrier 191 from escaping through the front end of the groove 196 in which it rides.

Figure 14:
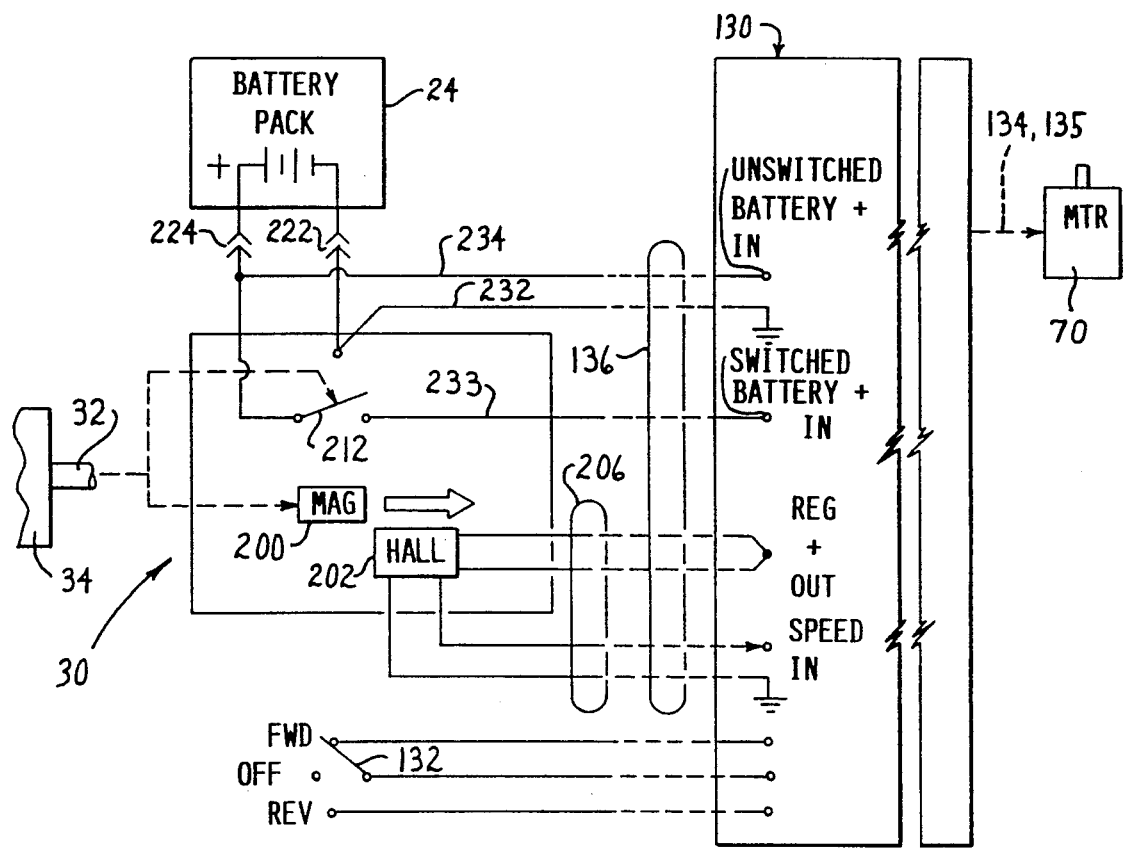
FIG. 14 is a simplified schematic view showing a simplified example of electrical connections of the forward/off/reverse switch 132, trigger unit 30 and battery pack 24 to the motor control unit 130.
Figure 13:
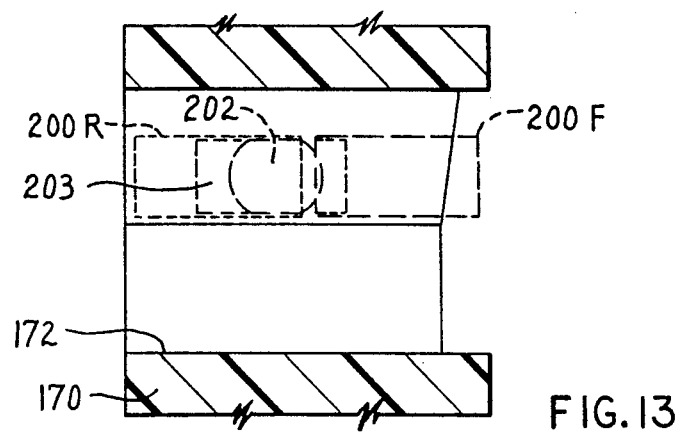
FIG. 13 is an enlarged fragmentary sectional view substantially taken on the line 13—13 of FIG. 9.

A permanent magnet 200 is fixedly inset, in a flush manner, in the outer sidewall 201 (FIG. 10) of the carrier 191. A Hall sensor 202 is fixedly located in a chamber 203 located in the block sidewall 204 closest to and opposing the magnet 200. The chamber 203 opens through the outer face of the block sidewall 204. Insulated conductors 206 (here four conductors 206A, B, C and D) connect electrically to corresponding terminals of the Hall sensor and are led upward out of the chamber 203 and through snug, sealed holes in the top of the block 170. The Hall sensor 202 lies close to the bottom through hole 172 in the block 170 and is separated therefrom by only a thin wall 207 of the material of the block 170. The Hall sensor 202 is disposed along the path of travel of the magnet as schematically indicated in FIG. 14 and as further shown in FIGS. 12 and 13.

The front (off) and rear (maximum speed) positions of the magnet 200 with respect to the Hall sensor 202 are shown respectively in long broken lines at 200F and in shorter broken lines at 200R, these being the front and rear positions respectively of the magnet 200, respectively corresponding to no trigger retraction (e.g. FIGS. 1, 7, 11 and 12) and full trigger retraction.

In the embodiment shown, the chamber 203 is filled with a hardenable potting compound, not shown, which may be used to hold the Hall sensor 202 rigidly in place at the thin wall 207.

A camming pin 210 is fixed to and protrudes sidewardly from the interior side of the carrier 191 (FIGS. 8-10 and 12), i.e. in a direction away from the Hall sensor 203 and magnet 200, and toward the opposite, vertical sidewall (left sidewall in FIG. 10) 211 of the bottom through hole 172 of the block 170. A crank 212 is pivotally supported by a pivot pin (here hollow) 213 (FIGS. 10 and 12) fixed in a horizontal sidewardly extending hole 214 (FIG. 10) in the adjacent sidewall 215 (the left sidewall in FIG. 10) of the block 170.

As seen in FIG. 12, the crank 212 has front and rear legs 216 and 217 respectively. In the relaxed, off, forward position of the carrier 191 and its camming pin 210, shown in FIG. 12, the front leg is in front of the pivot pin 212 and extends downward, and the rear leg 217 extends rearward with a modest downward slope. The rear leg 217 has, on its rear end, a substantially upward and rearward angled foot 220. The crank 212 is a flat plate and the free end of the foot 220 is beveled at 221 toward its upper rear edge.

Upstanding, rigid, electrically conductive contact plates 222, 223 and 224 (FIGS. 8, 9 and 11) are fixed in corresponding rear facing grooves in the block 170 by suitable means, here including screws 225, 226 and 227 respectively. The conductive plates 222 and 224 protrude rearwardly from the block 170 for a substantial portion of their respective heights and these rearward protruding portions of the plates 222 and 224 constitute contacts which slidably receive and releasably electrically connect with the ground and positive terminals of the battery pack 24 as hereafter discussed, upon slidable insertion of the battery pack 24 up into the handpiece handle 13.

The plates 223 and 224, at about the height of the cylinder 175, fixedly support the upper ends of sinuously curved, electrically conductive leaf springlike switch contacts 230 and 231 respectively (FIG. 9). The lower end portions of the switch contact 230 here is always in contact with crank 212 and the contact 231 is spaced from the beveled end 221 of the foot 220 of the conductive crank 212 and does not make electric contact therewith in the rest (unactuated) position of the apparatus shown in FIGS. 9 and 12. However, as the user pulls the trigger member 34 and thereby pushes leftwardly (FIGS. 7 and 12) the trigger shaft 32, the carrier 191, as above mentioned, moves leftwardly in the block 170, so that the camming pin 210 displaces leftwardly therewith. Leftward displacement of the camming pin 210 causes it to ride leftwardly against the underside of the rear crank leg 217, thereby lifting the latter. This thereby raises the beveled upward facing end 221 of the foot 220 of the rear leg 217 until such time as the crank 212 and rear leg 217 and beveled foot end 221 pivot clockwise into their dotted line end positions of FIG. 12. In the progress from the full line to dotted line positions of FIG. 12, the beveled end 221 of the foot rises in FIG. 9 into contact with the closest spaced lower portions of the spring-like switch contact 231 to provide a reliable electrical connection between contacts 230 and 231, i.e. so that switch contacts 230 and 231 connect electrically to each other.

When the user releases the trigger, the spring 183 (FIG. 12) pushes the head 176 and hence the trigger shaft 32 back rightwardly toward its rest position shown, thereby moving the carrier 194 rightwardly. The pin 210 on the carrier thus also moves rightwardly along the bottom of the rear crank leg 217 until it hits the left edge of the front crank leg 216. The final rightward displacement of the carrier 191 causes the pin 210 thereon to positively counterclockwise rotate the crank 212 out of bridging electric contact between the two spring-like contacts 230 and 231 so that the latter are no longer in electrical communication with each other.

As seen in FIG. 8, insulated wires 232, 233 and 234 connect to the plates 222, 223 and 224 respectively.

FIG. 14 schematically illustrates the electrical connections above described between the battery pack 24, switch unit 30, forward/off/reverse switch 132, the motor control unit 130 and motor 70. FIG. 14 simply illustrates in schematic form that which has already been above described in connection with the structure drawings.

As above mentioned, the control unit 130 may be of any convenient type. If an unswitched source of positive battery voltage is needed in the controller 130, the line 234 can be used to supply it, whereas the line 233 supplies switch to battery positive voltage to the control unit 130. If the control unit 130 provides a regulated positive voltage, same can be used to supply the Hall sensor 202 in the trigger unit 30, in preference to an unregulated positive voltage such as the switched battery positive voltage on line 233. Two separate line here supply positive operating voltage to the Hall sensor although it is contemplated that just one such line may be used. A variety of prior control circuits are known and can be used as the control unit 130 in FIG. 14 or to otherwise control the actuation, deactuation and speed of the motor 70 from the battery pack 24, trigger unit 30 and forward/off/reverse switch 132. As mentioned above, one particularly advantageous example is shown in U.S. Pat. No. 5,136,220 assigned to the assignee of the present invention.

Figure 11:
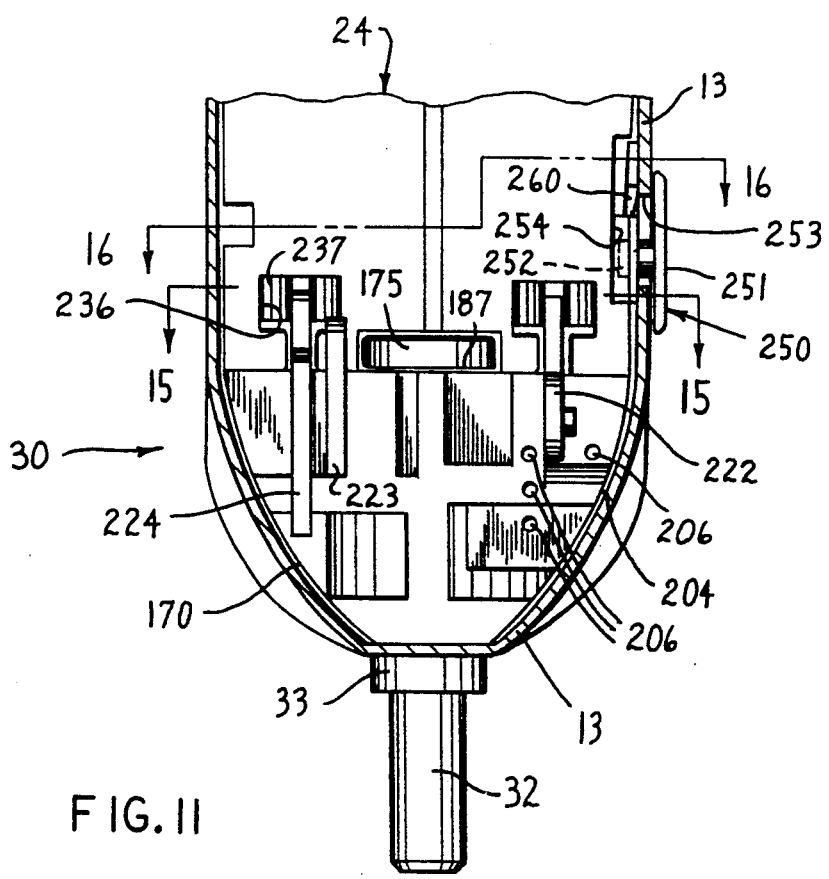
FIG. 11 is a top view of the FIG. 9 trigger unit.

To supply operating current to the battery terminal plates 222 and 224, upon insertion of the battery pack 24 into the housing handle 13 to its fully installed position of FIG. 7, the forward face of the battery pack 24 above the step 235 therein is provided with a transversely spaced pair of forward facing upwardly extending undercut grooves 236 (FIG. 11). Resilient, electrically conductive pairs of leaf spring contacts 237 (FIGS. 11 and 17) extend upward in the grooves 236 from terminals 239 and 240. The terminals 239 and 240 extend downward fixedly through the bottom wall 241 of their respective grooves 236 and into the closed chamber 242 in which battery cells (not shown) of any convenient type are housed and provide positive and negative battery terminals, schematically indicated in FIG. 15, electrically connected to the positive and ground terminals 239 and 240. Thus, sliding the battery pack 24 upward into the open bottom of the handle 13 causes the leaf spring contacts 237 of the positive and ground terminals 239 and 240 to respectively slide up along and electrically engage the positive and ground terminal plates 224 and 222 protruding rearward from the trigger unit 30. Thus, with the battery pack fully inserted up into the handle, a substantial portion of each of the terminal plates 222 and 224 is housed in its corresponding undercut groove 236 in the upper front wall of the battery pack.

Suitable latch means of resiliently engageable, manually disengageable type may be used to prevent unintended dropping of the battery pack 24 from the bottom of the handle 13. In the particular embodiment shown, for example, a thumb button 250 is movable substantially horizontally on the outside of the left side of the handle 13 (left side as seen looking forwardly). The thumb button 250 comprises a head 251 (FIG. 16) slidable horizontally along the outside of the handle 13 and a shank 252 extending inboard from the head 251 horizontally inboard through a horizontally extending slot 253 in the side of the handle 13 and into a groove 254 in the adjacent face of the battery pack 24. The groove 254, as seen from the side in FIG. 17, is generally J-shaped, having a vertical leg 255 extending up through the top of the battery pack 24 with a leftwardly (forwardly) extending, somewhat upsloped, bottom leg 266. Suitable means forwardly (leftwardly in FIG. 18) resiliently urge the thumb button shank 252 forwardly (leftwardly in FIG. 17) with respect to the handle 13.

For example, in the embodiment shown, such biasing means comprise an elongated leaf spring 260 having a top end 261 fixed by any convenient means, such as welding, to the inside of the handle 13 at a distance above the slot 253, having a mid portion 262 which extends generally downward and having a bottom end 263 which is fixed, by any convenient means such as welding, to the side of the shank 252 of the thumb button 250, all as generally indicated in FIGS. 16 and 17. The spring 260 is mounted in a manner to forwardly urge the shank 252 of the thumb button 250. In the embodiment shown, the mid portion 262 of the spring 260 is inset a bit from the inside surface of the handle 13 but by a small enough amount that the leaf spring 260 and shank 252 of the thumb button can be received into the side facing vertical leg 255 of the groove 254 in the battery pack 24 as the battery pack is inserted upward into the open bottom of the handle 13. The upper end of the vertical leg 255 of the groove 254 includes a forward and upward sloping ramp 265 that helps guide the forwardly urged thumb button shank 252 rearward into the groove 255 as the upper end of the battery pack 24 completes the first part of its entry into the handle 13. See for example the dotted line indications in FIG. 17. Further upward travel of the battery pack 24 into the handle 13 causes the thumb button shank 252 to ride along the vertical groove leg 255 of the groove 254 toward the bottom thereof. As the battery pack 24 nears its uppermost, fully inserted position in the handle 13, the thumb button shank 252 reaches the leg 266 of the battery pack groove 254 and is pushed forward by its spring 260 into such groove leg 266, as seen in FIG. 17. In this position, the thumb button shank 252 positively prevents the battery pack 24 from being drawn downward out of, or falling downward out of, the open bottom of the handle 13. In other words, the battery pack 24 is now positively locked in its fully inserted position in the handpiece handle 13.

To unlock the battery pack 24 from the handle 13, the operator manually pushes the thumb button head 251 rearward (rightward in FIG. 18) against the bias of its spring 260 and into the bottom portion of the vertical leg 255 of the battery pack groove 254. In that position, the thumb button shank 252 no longer interferes with the top 266 of the battery pack groove bottom leg 256 and thus allows the battery pack 24 to be pulled downward out of the open bottom of the handpiece handle 13.

OPERATION

The operation of the disclosed apparatus has been indicated in detail above. However, for convenient reference, same is briefly reviewed below.

To assemble the handpiece 10, the trigger unit 30 is inserted into the handle 13 with its shaft 32 protruding forward through the corresponding hole in the front wall of the handle 13 and the collar 185 (FIG. 12) is sleeved over the shaft 32 and threaded into the front end of the plunger assembly 174. The trigger member 34 is then fixed on the exposed forward end of the shaft 32. The electrical leads from the trigger unit 30 are long enough to be let out the open rear end of the barrel 12 for connection to the control unit 130 while the latter is still outside the barrel 12.

Thereafter, the preassembled cartridge 40, carrying the rear tube 121 and motor control unit 130, are inserted in the open rear end of the barrel 12 of the housing 11. The back cap 20 is sleeved over the rear tube 121 and inserted in the open rear end of the barrel 12. The nuts 54 and 142 are threaded onto the cartridge mid portion 53 and the rear tube 121 and tightened and the decorative cap 143 is added onto the rear end of the rear tube 121.

A given handpiece may be provided with one or more alternatively usable and rechargeable ones of the battery packs 24 to ready the handpiece 10 for use and provide electric operating power thereto. A battery pack 24 is inserted upward into the open bottom of the housing handle 13 into its position shown in FIG. 7. During the last portion of its movement into the handle, the rear extending plates 222 and 224 of the trigger unit are slidably and conductively received between corresponding pairs of the resilient, electrically conductive leaf spring contacts 237 of the battery pack 24. Upon full insertion, the battery pack 24 is held captive in the handle 13 by the shank 252 of the thumb button 250 on the left side of the handle 13 (left side as seen facing forward) along the barrel 12 toward the tool carrier (e.g. chuck) 23.

To allow replacement of the battery pack 24, the operator moves the thumb button 250 (and hence its shank 252) rearward to disengage same from the forward extending bottom leg 256 of the groove 254 in the left side of the battery pack 24, whereupon the battery pack could be pulled downward out of the handpiece handle 13, the thumb button shank 252 riding slidably in the vertical leg 255 of the groove 254 in the left side of the upper portion of the battery pack 24, so as to allow free removal of the battery pack 24 from the handpiece handle 13.

Prior to use, the handpiece 10 can be sterilized, as by high temperature steam in an autoclave. The motor 70 and speed reducer unit 100 (FIG. 2) are protected from contact by steam by the outer shell of the cartridge and by the front and rear seals 91 and 152. Moisture is kept out of the connections to the Hall sensor 202 in the trigger unit 30 by the thin wall 207 separating the Hall sensor from the slide magnet 200 and by conventional potting compound filling the chamber 203 outboard of the Hall sensor 202. The switch comprising contacts 230 and 231 and the crank 221 does not require a moisture-free environment, although a plate-like shield 246 (FIGS. 7 and 8) may be spaced to the rear of the switch elements to shield them somewhat from direct physical contact by solid objects, as for example during insertion of the battery pack 24 into the handle 13.

Electrical connections (not shown) in the control unit 130 may be protected against autoclave steam by conventional potting (not shown) as well.

Preferably after chucking a suitable tool (not shown) in the tool carrier 23, the user can operate the handpiece to provide operating movement to the tool member by pulling the trigger member 34 and thereby causing the trigger shaft 32 to move rearward into the cylinder 175 (FIG. 8) of the trigger unit 30. The carrier 191 (FIG. 8) moves rearward with the shaft 32, to which it is fixed. The pin 210 on the carrier 191 cams the crank 212 clockwise (FIG. 12) into contact with the switch contacts 230 and 231, electrically connecting the two to energize the motor control unit 130 from the battery pack 24. Continued rearward movement of the shaft 32 and thereby the carrier 191 moves the magnet 200 (FIG. 10) further along past the Hall sensor 202 (FIG. 13) so that the latter signals the control unit 130 to start and progressively increase the speed of the motor.

Conversely, as the user releases the trigger member 34, the shaft 32 and carrier 191 slide forward (rightward in FIG. 12) moving therewith the magnet 200 and causing the Hall sensor 202 (FIG. 10) to signal the control unit 130 for reduced motor speed. The camming pin 210 simultaneously slides forward along the underside of crank leg 217 until it reaches the crank leg 216 and pushes it forward from its dotted line position toward its solid line position in FIG. 12 such that the crank leg 217 no longer electrically connects the switch contacts 230 and 231, thereby opening (making non-conductive) the on/off switch defined by the crank 212 and contacts 230, 231.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A pistol-shaped surgical handpiece, comprising:
   a pistol-shaped housing including a forward/rearward extending barrel and a handle depending from said barrel;
   a motor supported in said barrel and having a rotatable motor shaft extending substantially axially forward along said barrel;
   a tool carrier located at the front end of said barrel and driven by a hollow output shaft;
   speed changer means for driving said output shaft and tool carrier from said motor shaft at a speed different from said motor shaft, said motor and speed changer means and tool carrier being aligned in said barrel, said motor and speed changer means having a continuous central passage therethrough extending to said tool carrier and defined by extension of said hollow output shaft axially through said motor and speed changer means.

2. The apparatus of claim 1 in which said barrel has a fixed rear end wall, said rear wall having a hollow fixed forward extension coupled to the rear end of said hollow output shaft, such that said continuous passage extends forward through said rear end wall coaxially through the length of said output shaft and through said tool carrier, said continuous passage permitting feeding of an elongate wire forward into the rear end wall of said barrel along the length of said barrel and out the front end thereof through said tool carrier to enable use of said handpiece as a wire driver.

3. The apparatus of claim 1 in which said rotatable motor shaft is hollow through its length, said hollow output shaft extending axially and relatively rotatably through said hollow motor shaft.

4. The apparatus of claim 1 in which the output shaft runs at a lower speed than the motor shaft, support means fixed within said housing behind said motor and through which said output shaft extends, a seal fixedly carried by said support means, and coaxially and sealingly engaging said output shaft to prevent entry of foreign matter through said output shaft into the interior of said housing, such that said seal engages the slower speed one of said shafts.

5. The apparatus of claim 1 in which said rotatable motor shaft is hollow through its length and is rotatable at a relatively high speed, said speed changer means driving said output shaft at a speed lower than the speed of said motor shaft, said output shaft extending axially through said hollow motor shaft, the output shaft interior communicating with the exterior of said housing, said motor shaft interior being isolated from the exterior of said housing.

6. A pistol-shaped surgical handpiece, comprising:
   a pistol-shaped housing including a forward/rearward extending barrel and a handle depending from said barrel;
   a motor supported in said barrel and having a rotatable shaft extending substantially axially forward along said barrel;
   a tool carrier located at the front end of said barrel and means for driving said tool carrier from said rotatable motor shaft, said rotatable motor shaft being hollow through its length and rotatable at a first speed, said driving means comprising speed changer means located in said barrel between said motor and tool carrier, said driving means further comprising an output shaft for driving said tool carrier from said speed changer means at a second speed, different from said first speed of said motor shaft, said output shaft extending axially through said hollow motor shaft.

7. The apparatus of claim 6 in which the output shaft runs at a lower speed than the motor shaft, support means fixed within said housing behind said motor and through which said output shaft extends, a seal fixedly carried by said support means and coaxially and sealingly engaging said output shaft to prevent entry of foreign matter through said output shaft into the interior of said housing, such that said seal engages the slower speed one of said shafts.

8. The apparatus of claim 7 including a rear tube fixed with respect to said barrel and extending coaxially rearward out the rear end of said housing from said output shaft to create therewith a passage extending the entire length of the barrel and opening through the rear end of the barrel and front end of said tool carrier to allow insertion of a wire therethrough, said seal being adjacent said rear tube and also preventing foreign matter in said tube from entry into the housing interior.

9. A pistol-shaped surgical handpiece, comprising:
a pistol-shaped housing including a forward/rearward extending barrel and a handle depending from said barrel;
a motor supported in said barrel and having a rotatable shaft extending substantially axially forward along said barrel;
a tool carrier located at the front end of said barrel and means for driving said tool carrier from said rotatable motor shaft;
a cartridge having a rigid hollow circular cross section casing removably insertable in said barrel, said motor and driving means being precisely coaxially piloted in said cartridge casing for insertion as a part of said cartridge into said barrel, whereby said motor and driving means can be run for test purposes while in said cartridge casing and prior to installing the cartridge in said barrel, said motor and drive means being precisely located with respect to each other independent of, and without need to precisely form, the barrel.

10. The apparatus of claim 9 in which said handle is hollow and opens at the bottom, a battery, the upper major length portion of said battery being removably upward insertable in said handle through said open handle bottom, the lower minor length portion of said battery depending from the bottom of said handle, releasable latch means for releasably retaining said battery in said handle.

11. The apparatus of claim 9 in which said barrel is of irregular form and of rigid but thin walled material, said barrel having front and rear openings of respectively lesser and greater size, said cartridge being received in the rear opening of said housing, a circular front sleeve fixed in said front opening and snugly but axially slidably receiving a front portion of said cartridge therethrough, a front nut threaded on said cartridge front portion and rearwardly abutting said sleeve to positively block rearward movement of said cartridge in said housing, a rear tube extending coaxially rearward from a rear facing wall of the cartridge, a back cap engageable with the rear end of said barrel to close same and having a central opening through which said rear tube extends snugly, a rear hut threaded on said rear tube outside said back cap and tightenable thereagainst to axially tension said cartridge and rear tube and axially pressure said barrel and rear cap.

12. The apparatus of claim 11 in which said cartridge comprises a rigid hollow elongate shell with hollow plugs fixed at the front and rear ends, said rear tube having an outer flange at the front end for attachment ahead of said rear plug, a hollow control unit sleeved on said rear tube behind said rear plug and in front of said barrel rear cap, said front sleeve axially abutting a front facing step on said front plug of said cartridge.

13. The apparatus of claim 9 in which the barrel loosely surrounds said cartridge and including front and rear axially spaced fixing means for effectively floating said cartridge loosely in said barrel.

14. A powered surgical handpiece comprising:
a handpiece housing;
means in the housing for imparting a desired movement to a tool;
a trigger unit mounted in the housing and having a trigger member movable by the finger of the user of the handpiece, the trigger unit comprising:
on/off switch means responsive to movement of said trigger member in a first direction for enabling motion of the tool;
speed control means responsive to movement of said trigger member in said first direction for increasing the speed of movement of said tool, said on/off switch means and speed control means being arranged such that said on/off switch means assures disabling of all movement of said tool upon completion of movement of said trigger member in the opposite direction, even if said speed control means should fail to select a zero speed setting.

15. The apparatus of claim 14 in which said trigger unit includes a carrier fixed with respect to said trigger member and movable therewith with respect to the housing, said on-off switch means and said speed control means being responsive to movement of said carrier with respect to said housing.

16. The apparatus of claim 14 in which said speed control means includes a permanent magnet fixed on said carrier and means fixed with respect to the housing adjacent the path of the magnet for providing a speed signal in response to movement of said magnet therepast.

17. The apparatus of claim 15 in which said on/off switch means includes an on/off switch contact fixed with respect to said housing near said carrier, a pivot member pivoted on an axis fixed with respect to said housing and having a camming edge, a camming element on said carrier engageable with said camming edge on said pivot member for pivoting said pivot member into engagement with said switch contact upon advance of said trigger member.

18. The apparatus of claim 17 in which said pivot member is a crank having first and second arms, said camming edge being on said first arm, said first arm having an end engageable with said switch contact, said camming element on said carrier comprising a pin engageable with the second leg of said crank upon retraction of said trigger member for positively disengaging said crank member from said switch contact.

19. The apparatus of claim 14, in which the housing includes a handle, a battery removably received within the handle of the handpiece housing, the trigger unit being fixed at the upper front portion of the handle, the upper front corner of the battery being notched to make room for the trigger unit, slidably interengageable tongue and groove electrical connection means of complementary type on said battery and trigger unit, such that upon insertion of said battery into said handle, electrical connection is made between said battery and trigger unit.

20. The apparatus of claim 19 in which said trigger unit has a pair of rearwardly protruding, laterally spaced, blade-like electrical contacts constituting the tongue part of said tongue and groove means, said battery in its notched front wall having a corresponding and complementary pair of electrically conductive groove defining means defining the groove portion of said tongue and groove connection means, said blade-like electrical contacts and electrically conductive groove defining means extending in the insertion/removal direction of the battery with respect to the handle, such that upon insertion of the battery into the handle, the battery electrically conductive groove defining means slide along and receive the blade-like electrical contacts of the trigger unit.

21. A pistol-shaped surgical handpiece, comprising:
   a pistol-shaped housing including a forward/rearward extending barrel and a handle depending from said barrel;
   a motor supported in said barrel and having a rotatable shaft extending substantially axially forward along said barrel;
   a tool carrier located at the front end of said barrel and means for driving said tool carrier from said rotatable motor shaft;
   a battery, said handle being hollow and open at the bottom, said battery being upwardly insertable into the open bottom of the handle;
   releasable latch means coactive between said handle and battery for positively retaining said battery in said handle, said latch means including first means permitting longitudinal sliding of said battery into said handle, second means responsive to complete seating of said battery in said handle for positively latching said battery in said handle, third means manually displaceable with respect to said handle for releasing said battery from said handle.

22. The apparatus of claim 21 in which said first means comprises an open top longitudinal groove in the side of the battery and a latch element carried on said handle for riding in said groove as said battery enters the handle, said second means comprises a transverse groove in the side of said battery open to the bottom portion of said longitudinal groove and resilient means on said handle for urging said latch element from said longitudinal groove into said transverse groove as said battery reaches its fully inserted position in said handle, and said third means comprises a manually engageable button accessible outside said handle and shiftable for returning said latch element from said transverse groove to said longitudinal groove and therewith allowing withdrawal of the battery from the handle.

* * * * *

UNITED STATES PATENT AND TRADEMARK OFFICE
CERTIFICATE OF CORRECTION

PATENT NO. : 5,207,697
DATED : May 4, 1993
INVENTOR(S) : Steven J. Carusillo, et. al.

It is certified that error appears in the above-indentified patent and that said Letters Patent is hereby corrected as shown below:

On the Title page, item [73] Assignee: change "Kalamazaoo" to --Kalamazoo--.

Column 16, line 24, delete the ",".

Column 17, line 51, change "hut" to --nut--.

Signed and Sealed this

First Day of February, 1994

*Attest:*

BRUCE LEHMAN

*Attesting Officer*     *Commissioner of Patents and Trademarks*